(12) United States Patent
Cha

(10) Patent No.: US 6,210,907 B1
(45) Date of Patent: Apr. 3, 2001

(54) MEASURING DEVICE WITH ELECTRODES FABRICATED ON POROUS MEMBRANE SUBSTRATE IN WHOLE

(75) Inventor: Geun-Sig Cha, Seoul (KR)

(73) Assignee: Samduck International Corporation, Seoul (KR)

( * ) Notice: Subject to any disclaimer, the term of this patent is extended or adjusted under 35 U.S.C. 154(b) by 0 days.

(21) Appl. No.: 09/381,788

(22) PCT Filed: Mar. 26, 1998

(86) PCT No.: PCT/KR98/00064

§ 371 Date: Sep. 22, 1999

§ 102(e) Date: Sep. 22, 1999

(87) PCT Pub. No.: WO98/44342

PCT Pub. Date: Oct. 8, 1998

(30) Foreign Application Priority Data

Mar. 31, 1997 (KR) .................................................. 97-11956

(51) Int. Cl.⁷ .................................................. G01N 33/53
(52) U.S. Cl. .............................. 435/7.1; 435/4; 435/7.72; 435/11; 435/962; 422/68.1; 422/69; 422/70; 422/82.01; 422/82.02; 422/255; 422/261; 436/501; 436/518; 436/524; 436/528; 436/529; 436/530; 436/71; 436/806; 204/400; 204/403
(58) Field of Search .............................. 422/68.1, 69, 70, 422/82.01, 82.02, 255, 261; 435/4, 7.1, 7.72, 11, 962; 436/501, 518, 524, 528, 529, 530, 71, 806; 204/400, 403

(56) References Cited

U.S. PATENT DOCUMENTS

| 4,956,275 | * | 9/1990 | Zuk et al. . | |
|---|---|---|---|---|
| 5,395,504 | * | 3/1995 | Saurer et al. . | |
| 5,403,745 | * | 4/1995 | Ollington et al. . | |
| 5,516,644 | * | 5/1996 | Yamauchi et al. . | |
| 5,545,519 | * | 8/1996 | Vadgama et al. . | |
| 5,580,794 | * | 12/1996 | Allen . | |
| 5,682,884 | * | 11/1997 | Hill et al. . | |
| 5,695,947 | * | 12/1997 | Guo et al. . | |
| 5,753,519 | * | 5/1998 | Durst et al. | 436/518 |
| 5,756,362 | * | 5/1998 | Durst et al. | 436/518 |
| 5,789,154 | * | 8/1998 | Durst et al. | 435/6 |
| 5,837,546 | * | 11/1998 | Allen et al. . | |
| 5,939,331 | * | 8/1999 | Burd et al. | 436/518 |
| 5,958,791 | * | 9/1999 | Roberts et al. | 436/514 |
| 6,008,059 | * | 12/1999 | Schrier et al. | 436/518 |

OTHER PUBLICATIONS

Durst et al. (1992). Development of liposome–enhanced immuno–biosensing devices for field measurements of toxic substances. 2nd Bioelectroanalytical Symposium, Akademiai Kiado, Budapest. pp. 15–32.*

* cited by examiner

Primary Examiner—Long V. Le
Assistant Examiner—Minh-Quan K. Pham
(74) Attorney, Agent, or Firm—Bachman & LaPointe, P.C.

(57) ABSTRACT

The present invention relates to a measuring device which comprises electrodes fabricated on porous membrane substrate in which the sample migrates chromatographically; and the method of quantifying material in the sample by using the device. The sample material for measuring can be quantified by the measuring device of this invention, which is consists pretreatment bands in the lower part of porous membrane substrate and electrodes in the upper prt of pretreatment bands, by the procedure as foolows: The sample material for measuring is chromatographically migrated in the porous membrane substrate by applying the sample on the lower part of the porous membrane substrate; and then the changes of electric signal by the material at the electrode are measured to quantify the material. The analyzing method using the measuring device of this invention has merits that no additional preparation of the sample is needed, simple analyzing process, quantitative analysis of the material in a short time, and the economical efficiency because of the dispensability of skilled personnel due to easy manipulation.

15 Claims, 6 Drawing Sheets

MEASURING DEVICE WITH ELECTRODES FABRICATED ON POROUS MEMBRANE SUBSTRATE IN WHOLE

BACKGROUND OF THE INVENTION

The present invention relates to a measuring device with electrodes on porous membrane substrate in which the sample migrates chromatographically; and the method of quantifying material in the sample by using the device.

More specifically, this invention relates to a measuring device with pretreatment bands in the lower part of porous membrane substrate; and electrodes in the upper part of pretreatment bands.

The method of quantifying contains processes as follows: the sample material for measuring is chromatographically migrated in the porous membrane substrate on applying the sample by the lower part of the porous membrane substrate; and then the changes of electric signal (i.e. current, potential, conductivity, etc.) by the material at the electrode is measured to quantify the material.

Recently, the need of quantification of organic/inorganic species in the sample is increasing for the purposes of diagnosing and preventing diseases, adjusting processes in food and industrial chemistry field or analyzing pollutants.

Firstly, measuring the concentration of small amount of organic/inorganic species is carried out by chemical methods; for example, iron salt-sulfuric acid reaction or p-toluene salt-sulfuric acid reaction, which are used in quantifying cholesterol in blood. However, there are demerits in using these methods, because the above reactions are very sensitive to the experimental condition, requires large amounts of sample, and suffers from a severe interference. Thus, other methods such as immunological method using antibody or enzymatic method are often employed these days. These methods are extensively used because of the small amount of the sample, superior selectivity and accuracy, and also the ease of its manipulation.

Since immunological or enzymatic methods cannot give direct results, the concentration measurement is observed with fluorometry, colorimetry, spectrometry and electrochemical method using electrodes.

Among these methods, the chromatographic method using porous membrane substrate (i.e. nitrocellulose papers, filter papers and so on) can separate or remove the interfering material during the migration due to capillary phenomenon by the measuring sample. Additionally, various substrates in which the sample is pretreated are easily fabricated with this method. Therefore, it has been extensively used in various fields such as pregnancy diagnosis kit, cholesterol sensor, and so forth. However, the chromatographic method using porous membrane substrate is not suitable for quantitative analysis, because it is mainly used in qualitative analysis by observing the change of color or tint by the naked eye.

Recently, the method using sensor with electrodes is widely used in analyzing and measuring the material. The method is performed by measuring the changes of the material resulting from immunological or enzymatic reaction electrically through electrodes. This method has merits of superior selectivity and accuracy. But it also has demerits of the inability to pretreat the sample due to the difficulties in employing pretreatment band. In order to quantify the material by electrodes, the sample is adjusted beforehand to be applicable to the electrometer, and then it is applied to electrometer. However, complicated analyzing steps and requirement of skilled personnel remain as the problems of this method.

SUMMARY OF THE INVENTION

The present invention, which is presented to solve the above mentioned problems, intends to provide a measuring device which comprises porous membrane and electrode in whole, and so the pretreatment of the sample, which is an indispensable step in quantifying the material, and the quantification of the material by electrometer can be conducted in one system.

The present invention intends to provide the method of quantifying material in the sample by using the device.

DESCRIPTION OF THE PREFERRED EMBODIMENTS

Figure 1:
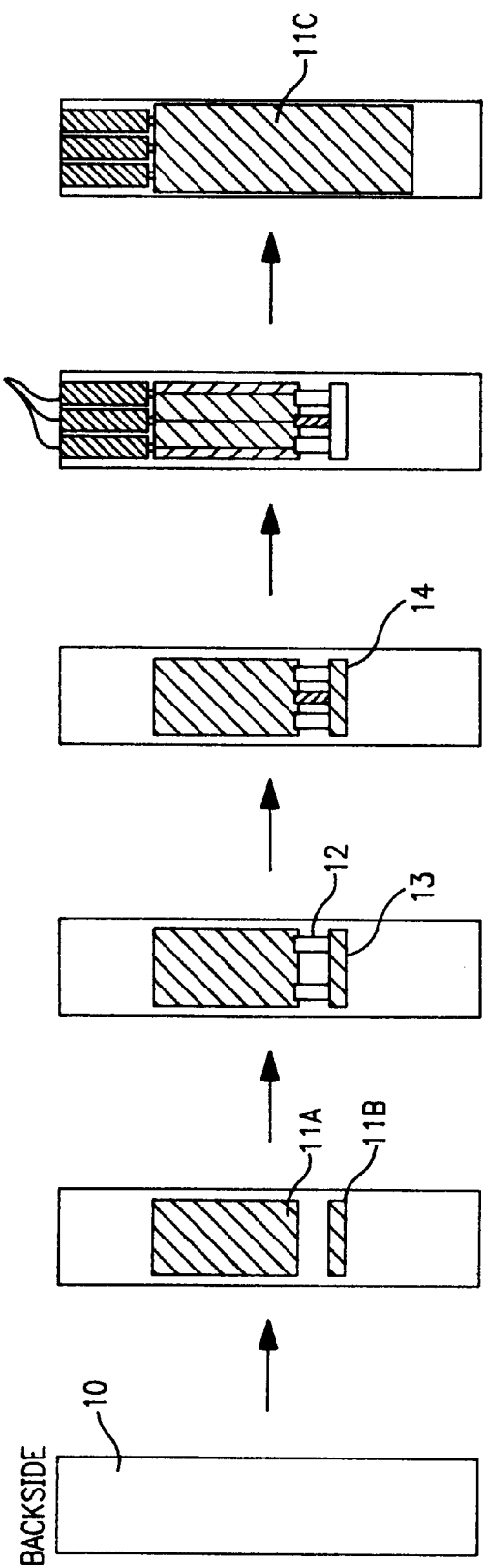
FIG. 1 is a scheme of process for preparing amperometric electrodes fabricated on porous membrane substrate.

The invention has characteristics of carrying our the pretreatment and quantification of the material simultaneously. That is, pretreating the sample in pretreatment bands which are in the lower part of porous membrane substrate, and quantifying the pretreated material in the electrodes which are in upper part of porous membrane substrate, by measuring the change of electric signal.

All kinds of porous membrane substrate which make the sample material migrate chromatographically can be used in this invention. For example, paper such as nitrocellulose paper; filter papers; organic polymer such as hydrophilic polymer, etc.; and inorganic polymer such as hydroscopic ceramics are preferred and the most preferable one is nitrocellulose paper.

In the lower part of porous membrane substrate, various layers may be employed, such as a layer which removed the interferents from the sample; a layer which converts the sample to be detectable by electrode; a layer which provides the optimum conditions for the electrode to detect the material; and so on.

There are some kinds of the layer which remove the interferents from the sample such as the antibody layer in which various antigens in the sample are removed by reacting with antigens; ethylenediaminetetraacetic acid (EDTA) layer in which heavy metal is removed; enzyme layer which converts the sample to be detectable by electrode; and buffer/surfactant layer which provides the optimum condition for the electrode to detect the material.

Additionally, electrometers such as voltammetric, amperometric, potentiometric and conductance method electrometers may be used to read change of electric signal occurred in the electrodes fabricated on porous membrane substrate.

As for the preferred embodiment of the measuring device of this invention, the method for preparation and use of the electrometer fabricated on porous membrane substrate is described in detail.

As depicted in FIGS. 2A to 2D, the measuring device of this invention comprises porous membrane substrate 10; insulating layer 11A and 11B, which are attached to the center and lower part of porous membrane substrate 10. These layers prevent oxidation of connection pad 15 by penetration of the sample. There are working electrode 12, counter electrode 13 and reference electrode 14, which is fabricated at the edge of center part of insulating layer 11A; connection pad 15, which connects the above electrodes 12 to 14 with electrometer; and insulating layer 11C, which prevents the short of the above electrodes 12 to 14.

This measuring device of this invention will now be described in detail with reference to FIG. 1.

Process 1.

Firstly, insulating layer 11A and 11B are fabricated on porous membrane substrate 10, which comprises paper such as nitrocellulose paper, filter paper; organic polymer such as hydrophilic polymer; and inorganic polymer such as hydroscopic ceramic for preventing the oxidation of connection pad 15b penetrating of the sample.

Process II

Secondly, the working electrode 12 and counter electrode 13 are constructed on porous membrane substrate 10 using conducting carbon paste, modified conducting carbon pastes [e.g. heavy metal oxides such as ruthenium oxide ($RuO_2$) or organometallic aompounds such as cobalt (II) phthalocyanine] or noble metal pastes such as gold (Au), platinum (Pt). Afterwards, the reference electrode 14 is constructed on porous membrane substrate 10 using silver/ silver chloride. Electrodes 12 to 14 are fabricated at the edge of insulating layer 11A to slightly overlap the edge and to be formed right on the porous membrane substrate 10, so that the sample can react by penetrating it.

Process III and IV

Connection pad 15 is made with silver, etc., for connecting the electrodes to the electrometer, and then the insulating layer 11C wraps the connection pad 15 to prevent the short of electrodes.

In each process, the components are formed by screen printing method, and then, densified by heat treatment, for example, at 50 to 150° C. for 15 to minutes.

Figure 2A:
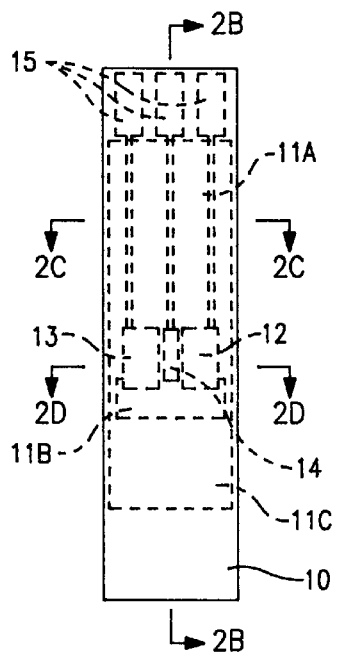
FIG. 2A is a front view of the amperometric electrodes prepared by process depicted in FIG. 1.
Figure 2B:
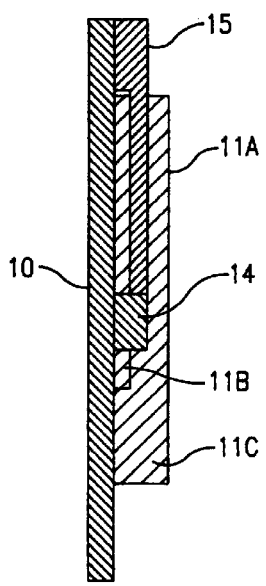
FIG. 2B is a cross-sectional view along the line 2B–2B' of FIG. 2A.
Figure 2C:
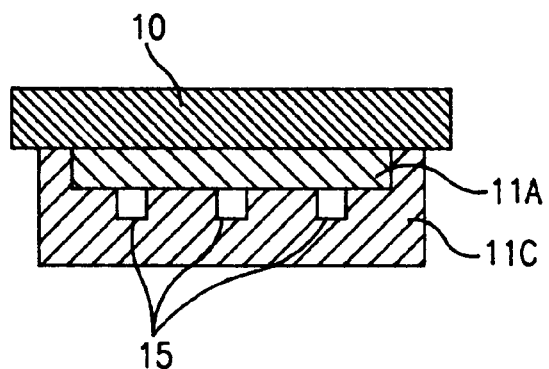
FIG. 2C is a cross-sectional view along the line 2C–2C' of FIG. 2A.
Figure 2D:
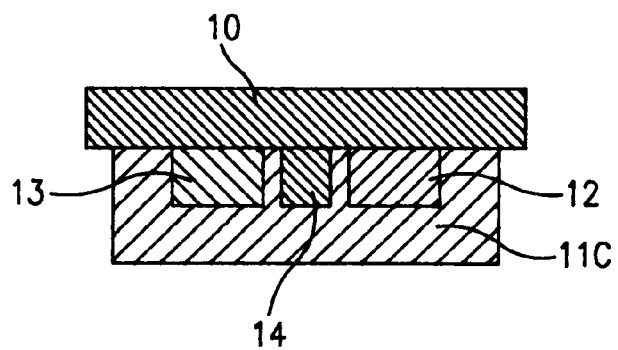
FIG. 2D is a cross-sectional view along the line 2D–2D' of FIG. 2A.

FIG. 2A is a front view of the measuring device by the process which is depicted in FIG. 1, FIG. 2B is a cross-sectional view along the line A–A', FIG. 2C is a cross-sectional view along line B—B;, and FIG. 2D is a cross-sectional view along line C–C'. As illustrated in the FIGS. 1 and 2, oxidation of connection-pad 15 by penetration of the sample is prevented because connection pad is wrapped up from top to bottom with insulating layer 11A and 11C. The sample material for measuring migrates from porous membrane substrate to electrodes by capillary phenomenon.

A detailed description of quantifying the sample material with the measuring device of this invention follows, taking the measurement of cholesterol concentration in blood as an example. Quantifying cholesterol is only one example and various other materials may be quantified in accordance with various layers.

Cholesterol consists of high density lipoprotein (HDL), low density lipoprotein (LDL) and very low density lipoprotein (VLDL). The higher the concentration of HDL in blood, the lower the attacking rate of disease relevant to blood vessel such as arteriosclerosis, myocardial infarction, and so on. However, it is known that the higher the concentration of LDL in blood, the larger the accumulation of thrombus and fat in blood and the higher attacking rate of arteriosclerosis. Thus, measuring LDL or HDL concentration in blood for diagnosing the diseases such as arteriosclerosis is a necessity. In order to determine LDL cholesterol concentration in blood, HDL and VLDL in blood are removed beforehand with enzyme, which selectively reacts with HDL and VLDL, and then LDL concentration is measured. Also, HDL is determined after removing LDL and VLDL using the enzyme which is selective to LDL and VLDL.

The method for determining LDL concentration in blood comprises processes as follows:

HDL and VLDL in blood are removed using HDL and VLDL antibody;

LDL is converted to cholesterol ester by surfactant; cholesterol is obtained by hydrolysis of cholesterol ester by cholesterol esterase (CED); H2O2 and cholesterol-4-en-3-one are generated from the reaction of cholesterol and cholesterol oxidase (COD);

and the electric signal is generated from redox reaction of H2O2 and amperometric electrometer.

Figure 3:
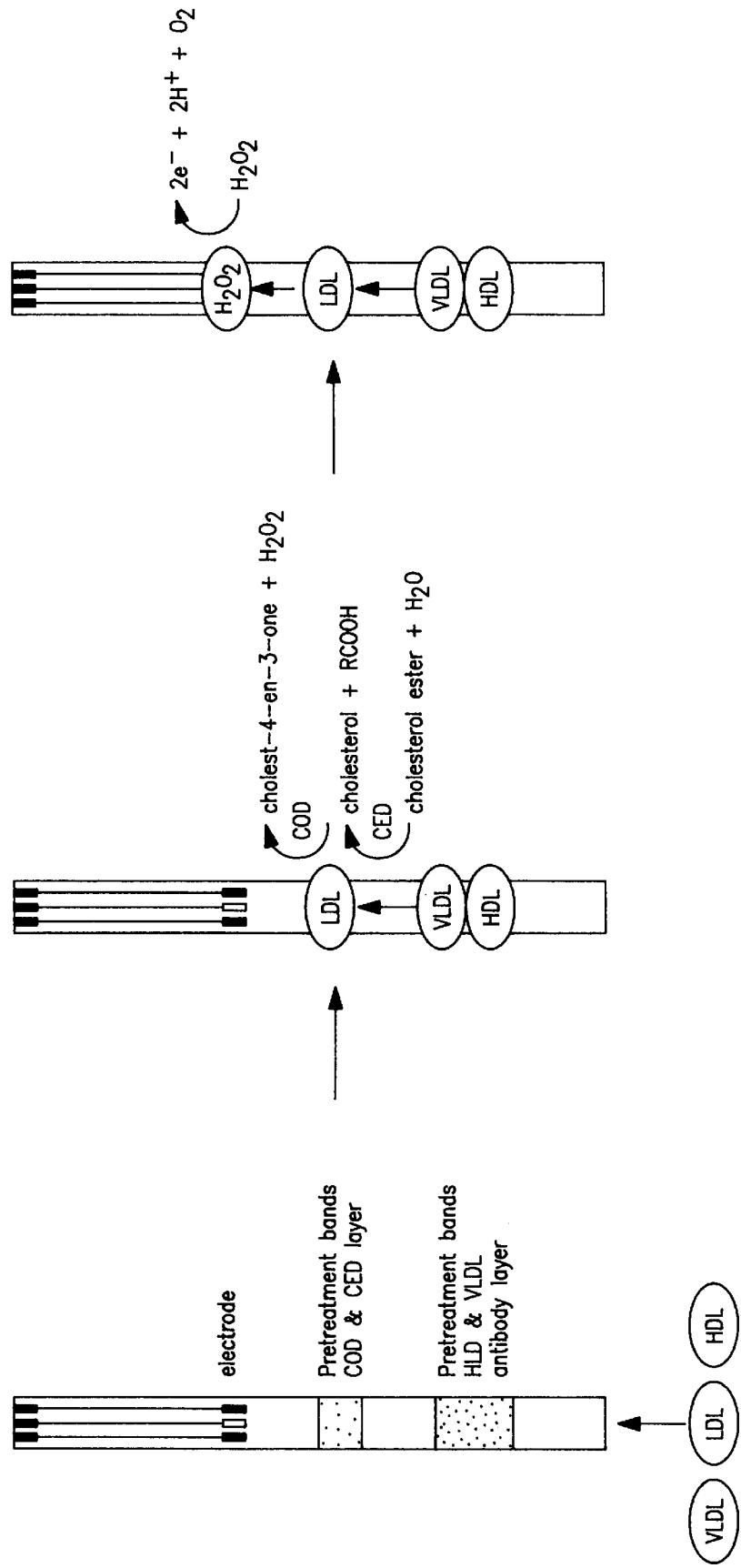
FIG. 3 is a structure of amperometric sensor for quantifying LDL cholesterol and its principle.

The above procedures are shown in Scheme I, and structure and reaction mechanism of the fabricated electrode are illustrated in FIG. 3. And, redox reaction of H2O2 is also shown in Scheme I.

Scheme I

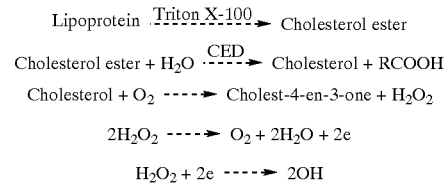

Concentration of various organic/inorganic materials in biosamples such as blood, urine;—environmental sample; industrial sample; or foodstuffs as well as that of cholesterol may be quantified by measuring changes of the electric signal in the electrode by material, which is pretreated in various layers fabricated on porous membrane substrate in accordance with various samples.

Figure 4:
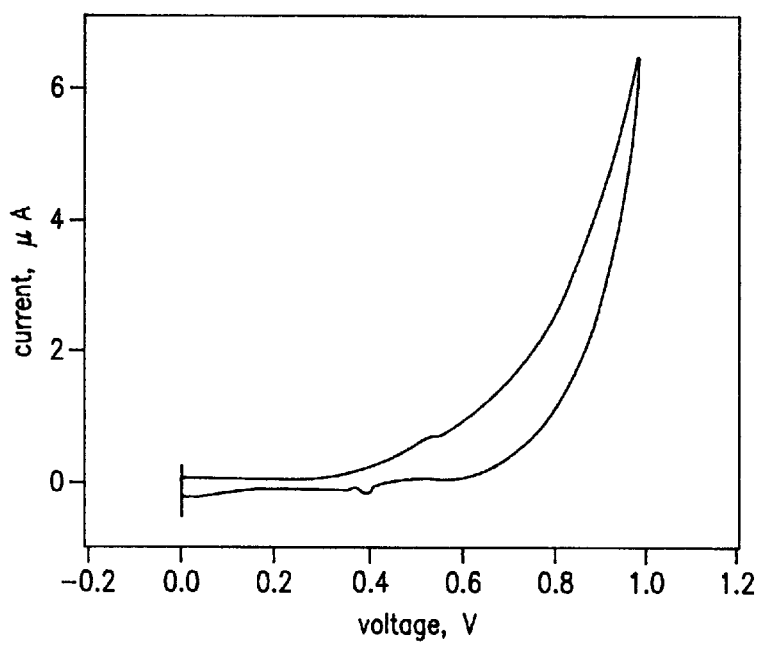
FIG. 4 shows a cyclic voltammogram of hydrogen peroxide($H_2O_2$) for a version of amperometric sensor, which comprises working electrode made of conductive carbon paste, fabricated on usual aluminum oxide substrate.

In order to confirm the applicbility of the measuring device of this invention which is consisted of electrodes, porous membrane substrate and soone, concentration of $H_2O_2$, one of the fianl products by enzymatic reaction was measured. Firstly, oxidation potential of amperometric sensor to $H_2O_2$ was measured and depicted in FIG. 4, which shows the cyclic voltammogram. The amperometric sensor is consisted of silver/silver chloride reference electrode and conductive carbonelectrode, which is fabricated on usual aluminum oxide substrate, as working and counter electrode. As a result of this measurement, it is apparent that $H_2O_2$ is oxidized from the upper level of 0.7 V.

Figure 5:
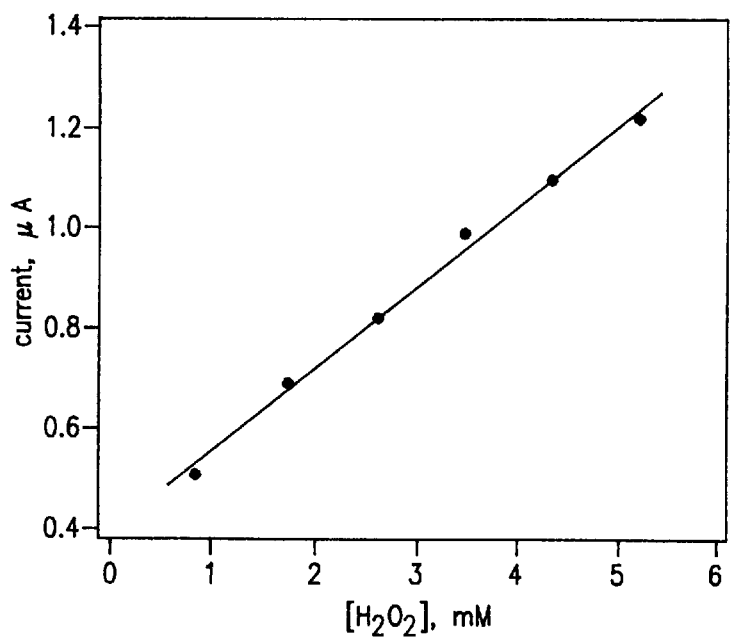
FIG. 5 shows a sensitivity to $H_2O_2$, and a calibration curve of a version of the amperometric sensor, which is fabricated on usual aluminum oxide substrate, to $H_2O_2$ at 0.7V in phosphate buffer solution (0.2 M, pH 7.0).
Figure 6:
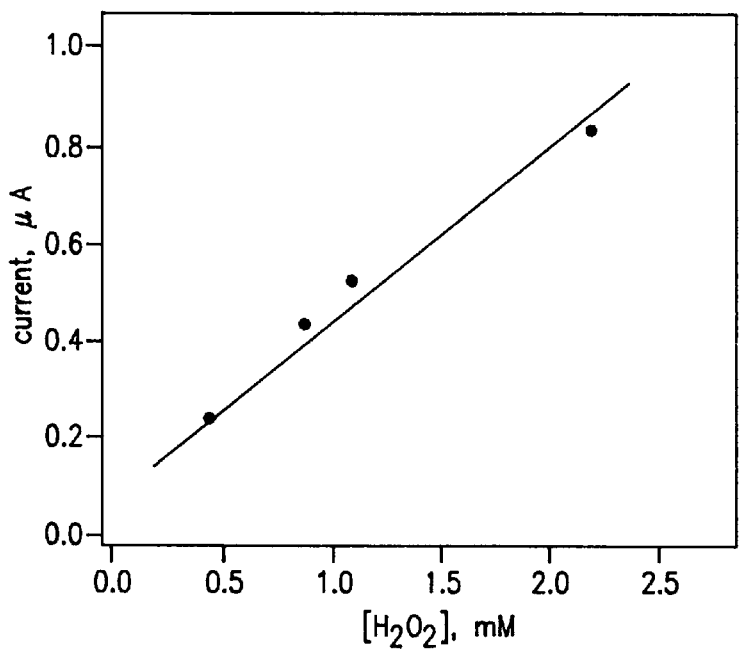
FIG. 6 shows a sensor to sensor sensitivity to H2O2, and a calibration curve at different H2O2 concentrations to each sensor of a version of the amperometric sensor, which is fabricated on porous membrane substrate, at 0.7 V and changing the concentration of H2O2.

Amperometric sensor using porous membrane substrate is not reusuable in determining the concentration of a material, and this differentiates the electrode shows by the calibration curve and the electrode determinng the concentration in actual application. Therfore, sensor to sensor reproducibility has a very important effect on the reliability of this sensor. In order to experiment sensor to sensor reproducibility, the sensor in which electrodes are fabricated on porous membrane substrate is compared with the sensor in which electrodes are fabricated on usual aluminum oxide substrate, then the reproducibility and sensitivity of the sensor are measured. (c.f. FIGS. 5 and 6).

FIG. 5 shows a calibration curve of a version of a sensor, which in fabricated on usual aluminum oxide substrate, and which consists of silver/silver chloride reference electrode and conductive carbon electrode as working electrode and counter electrode, at 0.7V. The calibration curve shows the results according to the changes of the concentration of the sample by adding 5u(micro)l of $H_2O_2$ (30%) in 50 ml of phosphoric acid buffer solution (0.2 M, pH 7.0). As apparent from FIG. 5, the calibration curve shows linearity in the range of 0.88 to 5.28 mM concentration.

FIG. 6 shows a calibration curve of a version of a sensor, which is fabricated on porous membrane substrate to H2O2. As apparent from FIG. 6, calibration curve has linearity in the range of 0.44 to 3.4 mM concentration, the major concerning range of concentration.

Comparing FIG. 5 with FIG. 6, linearity and sensitivity of the calibration curve in using the sensor in which various electrodes are fabricated on porous membrane substrate are very similar to those using the sensor in which an electrode is fabricated on aluminum oxide substrate. Therefore, reproducibility of the measuring device, which comprises electrodes fabricated on porous membrane substrate, has superior features.

(Effects of the Invention)

The analyzing method using the mesuring device of this invention has merits that no additional preparation of the sampel is needed, analyzing process being simplified, quantitative analysis of the material made possible in a short time, and that it is economical because of the dispensability of skilled personnel due to easy manipulation.

While thie invention has been described by reference to a specific example chosen for the purposes, it should be apparent that the present invention is not limited by the preferred embodiments.

EXAMPLE

I. Preparation of the Measuring Device

Electrodes were fabricated on the upper part of nitrocellulose paper, then pretreatment bands such as antibody layer, detergent layer and enzyme layer, were successively fabricated on the lower part of nitrocellulose paper. (c.f. FIG. 3)

1) Employing Pretreatment Bands

HDL and VLDL antibodies were employed as an antibody layer, and triton X-100, the surfactant, was employed as a detergent layer. Cholesterol esterase (CED) and cholesterol oxidase (COD) were employed as an enzyme layer.

2) Preparation of Electrodes

Insulating layer was constructed on nitrocellulose paper, then working and counter electrodes were fabricated with platinum (Pt) or conducting carbon, and silver/silver chloride reference electrode was fabricated on porous membrane substrate. These electrodes were connected to electrometer with silver, and wrapped up with the insulating layer.

II. Method for Quantifying LDL Cholesterol

Figure 7:
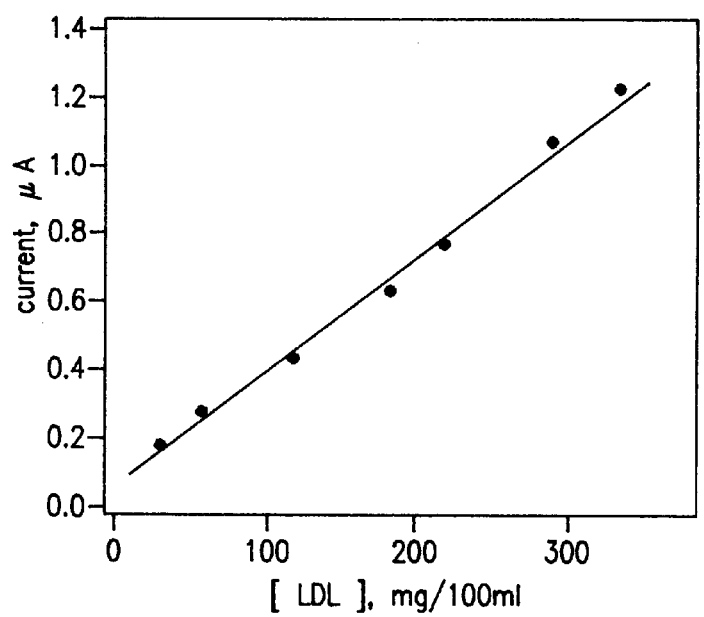
FIG. 7 shows a sensor to sensor sensitivity to LDL cholesterol in cholesterol, and a calibration curve at different LDL cholesterol concentration to each sensor of a version of the amperometric sensor, which is fabricated on porous membrane substrate, at 0.7 V and changing the concentration of LDL cholesterol.

Standard solution of cholesterol was dropped on the lower part of sensor, then the concentration of LDL cholesterol was quantified. FIG. 7 shows a calibration curve of LDL cholesterol in the total cholesterol in the sample in case of using the amperometric cholesterol sensor of this invention. As apparent from FIG. 7, the amperometric cholesterol sensor of this invention with various electrodes displayed linearity and reproducibility to LDL cholesterol in a range of to 350 mg/100 ml, which is range of the concentration LDL cholesterol in blood.

What is claimed is:

1. A measuring device which comprises a porous membrane substrate having a lower part, center part, and upper part in which a sample can migrate chromatographically from the lower part in the direction of the upper part; pretreatment bands constructed in the lower part of the porous membrane substrate; and electrodes constructed in the upper part of the porous membrane substrate, the electrodes comprise a working electrode, a counter electrode and a reference electrode, and a connection pad for connecting the electrodes with a circuit electrometer and having an insulating layer which prevents short circuit of the electrodes, wherein the porous membrane substrate is selected from the group consisting of nitrocellulose paper, filter paper, organic polymers comprising a hydrophilic polymer, and inorganic polymers comprising a hygroscopic ceramic and has first and second insulating layers provided in the center part and the lower part of the porous membrane substrate, respectively; the pretreatment bands comprise (1) a layer for removing interferents, (2) a layer for converting a sample material to be detected by the electrodes, and (3) a layer for detecting the sample material by the electrodes by at least one of controlling the pH and dispersing the sample material to be detected.

2. The measuring device of claim 1, wherein the electrodes are selected from the group consisting of voltammetric, amperometric, potentiometric and conductometric electrode system.

3. The measuring device of claim 1, wherein the layer for removing the interferents comprises at least one of an antibody layer and an ethylenediaminetetraacetic acid (EDTA) layer.

4. The measuring device of claim 1, wherein the layer for converting a sample to be detected by the electrodes comprises an enzyme layer.

5. The measuring device of claim 1, wherein the layer providing the optimum condition for the electrode comprises a buffer solution layer or a surfactant layer.

6. The measuring device of claim 1, wherein the working electrode is made of a material selected from the group consisting of conducting carbon pastes and modified conducting carbon pastes comprising at least one of heavy metal oxides, organometallic compounds, and noble metal pastes.

7. The measuring device of claim 6, wherein the heavy metal oxides is ruthenium oxide ($Ru_2O$), the organometallic compounds is cobalt (II) phthalocyanine and the noble metal pastes are pastes of gold and platinum.

8. The measuring device of claim 1, wherein the counter electrode is made of a material selected from the group consisting of conducting carbon pastes and noble metal pastes comprising at least one of gold and platinum.

9. The measuring device of claim 1, wherein the reference electrode is made of a material selected from the group consisting of silver, silver epoxy, silver/silver chloride, and silver/silver ion.

10. The measuring device of claim 1, wherein the pretreatment bands comprise (1) high density lipoprotein (HDL) and very low density lipoprotein (VLDL) antibody layers (2) a surfactant layer, and (3) cholesterol esterase (CED) and cholesterol oxidase (COD) enzyme layers.

11. Process for preparation of the measuring device of claim 1, which comprises forming the measuring device by screen printing in each step of the following steps:

(1) fabricating the first and second insulating layers on the porous membrane substrate to prevent the oxidation of the connection pad due to the penetration of a sample;

(2) constructing the working electrode and the counter electrode on the porous membrane substrate by using conducting materials, and constructing the reference electrode on the porous membrane substrate;

(3) constructing the connection pad by using conducting materials for connecting the electrodes to the electrometer;

(4) wrapping the connection pad with the third insulating layer to prevent the short circuit; and (5) constructing pretreatment bands on the porous membrane substrate.

12. The process for preparation of claim 1, wherein the process comprises a heat treatment step at 50 to 150° C. for 15 to 30 minutes after each of steps (1)–(4) for the densification of the materials of each component of the measuring device.

13. A method of quantifying by using the measuring device of claim 1 as a sensor, which comprises pretreating the sample in the pretreatment bands constructed in the lower part of the porous membrane substrate, and quantifying the pretreated material in the electrode part constructed in an upper part of the porous membrane substrate, by measuring the changes of electric signal.

14. The method of quantifying of claim 13, wherein the sample is selected from the group consisting of organic materials, inorganic materials, biosamples comprising blood and urine; environmental samples; industrial samples; and foodstuffs.

15. The method of quantifying of claim 14, wherein the pretreatment bands are selected from the group consisting of antibody layers, detergent layers and enzyme layers (CED and COD), and a method for determining LDL concentration is characterized by:

fixing HDL and VLDL in the blood in antibody layers, converting LDL to cholesterol ester during migration of detergent layers chromatographically, converting cholesterol ester to cholesterol by hydrolysis in CED, generating $H_2O_2$ and cholesterol-4-en-3-one by the reaction of the cholesterol and COD, and generating an electric signal by the redox reaction of $H_2O_2$ with amperometric electrometer.

* * * * *